United States Patent
Sicre et al.

(10) Patent No.: US 7,244,856 B2
(45) Date of Patent: Jul. 17, 2007

(54) PROCESSES FOR RECOVERING PHYTOSTEROLS VIA CRYSTALLIZATION

(75) Inventors: Christophe Sicre, Saint Gaudens (FR); Rene Armengaud, Boussens (FR); Joerg Schwarzer, Hilden (DE); Bernhard Gutsche, Hilden (DE); Markus Musholt, Stadtlohn (DE); Volkmar Jordan, Steinfurt (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 248 days.

(21) Appl. No.: 10/896,486

(22) Filed: Jul. 22, 2004

(65) Prior Publication Data

US 2004/0260104 A1 Dec. 23, 2004

Related U.S. Application Data

(63) Continuation of application No. 09/958,637, filed as application No. PCT/EP00/02849 on Mar. 31, 2000, now abandoned.

(30) Foreign Application Priority Data

Apr. 9, 1999 (DE) ............... 199 16 034

(51) Int. Cl.
*C07J 9/00* (2006.01)
(52) U.S. Cl. .................................... 552/545
(58) Field of Classification Search ................. 552/545
See application file for complete search history.

(56) References Cited

FOREIGN PATENT DOCUMENTS

GB 635497 * 4/1950

* cited by examiner

*Primary Examiner*—Barbara P. Badio
(74) *Attorney, Agent, or Firm*—John F. Daniels

(57) ABSTRACT

Processes for recovering phytosterols are described. The processes comprise: (a) providing a liquid mixture containing a phytosterol, methanol, and one or more additional compounds, wherein the methanol is present in an amount of from 25 to 75% by weight, based on the phytosterol; (b) cooling the mixture to form phytosterol crystals; and (c) separating the phytosterol crystals from the remainder of the mixture.

10 Claims, No Drawings

PROCESSES FOR RECOVERING PHYTOSTEROLS VIA CRYSTALLIZATION

CROSS-REFERENCE TO RELATED APPLICATIONS

This application claims priority under 35 U.S.C. §120, and is a continuation of U.S. patent application Ser. No. 09/958,637, filed on Jan. 14, 2002 now abandoned as a 35 U.S.C. §371 submission based upon International Application No. PCT/EP00102849, having an International Filing Date of Mar. 31, 2000, the entire contents of which are herein incorporated by reference.

BACKGROUND OF THE INVENTION

Phytosterols and their esters possess hypocholesterolaemic properties, i.e. these substances are capable of lowering the cholesterol level in the blood. Accordingly, they are used as food additives, for example for the production of margarine, frying oils, sausage, ice cream and the like. The production of sterols and other unsaponifiable constituents, such as tocopherols for example, from distillates obtained in the deacidification of vegetable oils, has already been variously described in the patent literature, cf. EP-A2 0 610 742 (Hoffmann-LaRoche), GB-A1 2,145,079 (Nisshin Oil Mills Japan) and EP-A1 0 333 472 (Palm Oil Research and Development Board).

European Patent EP-B1 0 656 894 (Henkel) describes a process for the production of sterols in which a residue from the distillation of methyl esters consisting essentially of glycerides, sterols, sterol esters and tocopherols is transesterified with methanol in the presence of alkaline catalysts. After neutralization of the catalyst, removal of the excess methanol by distillation and, optionally, removal of the catalyst by washing, the sterols are crystallized by lowering the reaction temperature from about 65 to 20° C. The crystals obtained are then washed with methanol and water. Unfortunately, the yield of sterols is unsatisfactory.

Accordingly, the problem addressed by the present invention was to provide phytosterols in high yields and to simplify existing known processes.

BRIEF SUMMARY OF THE INVENTION

The present invention relates, in general, to phytosterols for use in food additives, and more particularly, to a new, simplified process for the production of phytosterols.

It has surprisingly been found that the crystallization temperature of the sterols is significantly influenced by the methanol content in the reaction mixture. Thus, the melting temperature of a mixture with a methanol content of 30% by weight rises from 65 to 78° C. in relation to an alcohol-free fraction. Not only does this simplify the process and improve the energy balance, distinctly higher yields are also obtained in the subsequent working up phase. The invention includes the observation that the rise in the crystallization temperature is not a linear function of the methanol content because a rapid fall is observed at contents above about 75% by weight.

DETAILED DESCRIPTION OF THE INVENTION

Transesterification

The production of a sterol-rich fraction by transesterification of residues from the deacidification of vegetable oils and subsequent working up can be carried out as described in EP-B1 0 656 894. Suitable starting materials are the distillation residues obtained, for example, as so-called deodorizer condensates in the production of fatty acid methyl esters based on rapeseed oil or, more particularly, sunflower oil. Tall oil pitch, more particularly pitch obtained from birch bark, is also suitable. Where it relates to the production of the sterol fractions, reference is comprehensively made to the document cited above. The process is particularly suitable for the production of sterols based on vegetable oils which have only a small percentage content of $\alpha$-sitosterols. Accordingly, preferred starting materials are phytosterol-rich fractions from the transesterification of rapeseed oil ("rapeseed sterols") or soybean oil ("soya sterols").

Crystallization

The crystallization of the sterol fractions which, apart from the alcohol, mainly contain methyl esters takes place in known manner, i.e. the hot mixtures (ca. 90 to 100° C.) are slowly cooled to around 10° C. in a crystallizer. If necessary, alkaline catalyst from the transesterification present in the mixture can be neutralized beforehand, for example by addition of citric acid. According to the invention, only those mixtures which already have a ratio by weight of sterol to methanol of 100:25 to 100:75 from their production should be used. Otherwise methanol has to be added or distilled off. Under these conditions, the crystallization begins at temperatures of 75 to 80° C. It is of course also possible to use crude sterols instead of the transesterification products, to add methanol and optionally methyl ester and to concentrate the whole in the described manner. If desired, the crude sterols may also be washed with methyl ester fractions. Although, in this case, small amounts of product are lost, a lasting improvement in color is obtained. The phytosterols accumulating are then removed and purified in known manner, i.e. filtered off, washed free from esters and dried to constant weight.

EXAMPLES

Comparison Example C1

The starting material used was a rapeseed methyl ester fraction which, based on the content of free and bound sterols, additionally contained 100% by weight of methanol. The mixture was continuously cooled from ca. 100° C. to 10° C., the first crystals beginning to separate at 68° C. On completion of the crystallization, the crystals were filtered off, washed free from methyl ester with methanol and dried to constant weight. The yield was 78% by weight, based on the sterol content of the transesterification product.

Comparison Example C2

Example C1 was repeated using a mixture containing 200% by weight of methanol, based on the quantity of sterol. In this case, the crystallization only began at 63° C. and the yield was 72% by weight. In the form of a 10% by weight solution in ethanol, the products have a Hazen color number of 798 and a Gardner color number of 4.4.

Comparison Example C3

Example C1 was repeated using a mixture containing 300% by weight of methanol, based on the quantity of sterol. In this case, the crystallization only began at 56° C. and the yield was 68% by weight.

Example 1

Example C1 was repeated using a mixture containing 30% by weight of methanol, based on the quantity of sterol. The crystallization began at 78° C. and the yield was 92% by weight.

Example 2

100 g of a crude soya sterol mixture (sterol content: 83% by weight) were dissolved in 186 g of cocofatty acid methyl ester at 90° C. and methanol was added to the resulting solution in such a quantity that a ratio by weight of sterol to methanol of 2:1 was obtained. After the temperature had fallen, the first sterol crystals separated at 74° C. On completion of crystallization, the crystals were filtered off, washed free from methyl ester with methanol and dried. The resulting fraction had a purity of 93.7% by weight.

What is claimed is:

1. A process for recovering phytosterols, said process comprising:
    (a) providing a liquid mixture comprising a phytosterol, methanol, and one or more additional compounds, wherein the methanol is present in an amount of from 25 to 75% by weight, based on the phytosterol;
    (b) cooling the mixture to form phytosterol crystals, wherein the crystals are formed at a temperature of from 75 to 80° C.; and
    (c) separating the phytosterol crystals from the remainder of the mixture.

2. The process according to claim 1, wherein the methanol is present in an amount of from 30 to 50% by weight, based on the phytosterol.

3. The process according to claim 1, wherein the liquid mixture comprises a phytosterol-containing fraction produced via transesterification of an oil selected from the group consisting of rapeseed oil and soybean oil.

4. The process according to claim 2, wherein the liquid mixture comprises a phytosterol-containing fraction produced via transesterification of an oil selected from the group consisting of rapeseed oil and soybean oil.

5. The process according to claim 1, further comprising washing the separated phytosterol crystals with a fatty acid ester.

6. The process according to claim 2, further comprising washing the separated phytosterol crystals with a fatty acid ester.

7. The process according to claim 3, further comprising washing the separated phytosterol crystals with a fatty acid ester.

8. The process according to claim 4, further comprising washing the separated phytosterol crystals with a fatty acid ester.

9. A process for recovering phytosterols, said process comprising:
    (a) providing a phytosterol-containing fraction produced via transesterification of an oil selected from the group consisting of rapeseed oil and soybean oil, the fraction comprising a phytosterol, methanol, and one or more additional compounds, wherein the methanol is present in an amount of from 30 to 50% by weight, based on the phytosterol;
    (b) cooling the mixture to form phytosterol crystals, wherein the crystals are formed at a temperature of from 75 to 80° C.; and
    (c) separating the phytosterol crystals from the remainder of the mixture.

10. The process according to claim 9, further comprising washing the separated phytosterol crystals with a fatty acid ester.

* * * * *